United States Patent
Hoyle

(10) Patent No.: US 11,798,189 B2
(45) Date of Patent: Oct. 24, 2023

(54) COMPUTER IMPLEMENTED METHODS AND DEVICES FOR DETERMINING DIMENSIONS AND DISTANCES OF HEAD FEATURES

(71) Applicant: Carl Zeiss Vision International GmbH, Aalen (DE)

(72) Inventor: Ben Hoyle, Munich (DE)

(73) Assignee: Carl Zeiss Vision International GmbH, Aalen (DE)

(*) Notice: Subject to any disclaimer, the term of this patent is extended or adjusted under 35 U.S.C. 154(b) by 0 days.

(21) Appl. No.: 17/932,383

(22) Filed: Sep. 15, 2022

(65) Prior Publication Data
US 2023/0014102 A1    Jan. 19, 2023

Related U.S. Application Data

(63) Continuation of application No. PCT/EP2021/056528, filed on Mar. 15, 2021.

(30) Foreign Application Priority Data

Mar. 16, 2020   (EP) .................................. 20163342

(51) Int. Cl.
*G06K 9/00* (2022.01)
*G06T 7/70* (2017.01)
(Continued)

(52) U.S. Cl.
CPC .................. *G06T 7/70* (2017.01); *A61B 3/11* (2013.01); *A61B 5/107* (2013.01); *A61B 5/1079* (2013.01);
(Continued)

(58) Field of Classification Search
CPC ........ G06V 10/22; G06V 10/32; G06V 10/40; G06V 10/70; G06V 10/72; G06V 10/74;
(Continued)

(56) References Cited

U.S. PATENT DOCUMENTS

| 6,262,738 B1 | 7/2001 | Gibson et al. |
| 6,535,233 B1 | 3/2003 | Smith |

(Continued)

FOREIGN PATENT DOCUMENTS

| JP | 6392756 B2 | 9/2018 |
| WO | 2018002332 A2 | 1/2018 |

OTHER PUBLICATIONS

S. Bianco et al., "A unifying representation for pixel-precise distance estimation," Multimedia Tools and Applications, Kluwer Academic Publishers, Boston, US, vol. 78 No. 10, pp. 13767 to 13786, Aug. 24, 2018.

(Continued)

*Primary Examiner* — Eric Rush
(74) *Attorney, Agent, or Firm* — Tautz & Schuhmacher LLC; Georg M. Hasselmann

(57) ABSTRACT

Computer implemented methods and devices for determining dimensions or distances of head features are provided. The method includes identifying a plurality of features in an image of a head of a person. A real dimension of at least one target feature of the plurality of features or a real distance between at least one target feature of the plurality features and a camera device used for capturing the image is estimated based on probability distributions for real dimensions of at least one feature of the plurality of features and a pixel dimension of the at least one feature of the plurality of features.

13 Claims, 2 Drawing Sheets

(51) Int. Cl.
| | |
|---|---|
| *G06V 40/16* | (2022.01) |
| *A61B 5/107* | (2006.01) |
| *G06T 7/60* | (2017.01) |
| *A61B 3/11* | (2006.01) |
| *G06T 7/50* | (2017.01) |

(52) U.S. Cl.
CPC .............. *G06T 7/50* (2017.01); *G06T 7/60* (2013.01); *G06V 40/165* (2022.01); *G06V 40/168* (2022.01); *G06T 2207/20076* (2013.01); *G06T 2207/30196* (2013.01); *G06T 2207/30201* (2013.01); *G06V 2201/12* (2022.01)

(58) Field of Classification Search
CPC .... G06V 10/751; G06V 10/763; G06V 10/84; G06V 20/64; G06V 40/10; G06V 40/16; G06V 40/161; G06V 40/165; G06V 40/166; G06V 40/168; G06V 40/171; G06V 40/179; G06V 40/18; G06V 2201/12; G06T 7/50; G06T 7/60; G06T 7/62; G06T 7/70; G06T 7/73; G06T 7/97; G06T 2207/20076; G06T 2207/20228; G06T 2207/30196; G06T 2207/30201; A61B 3/1005; A61B 3/11; A61B 3/111; A61B 3/112; A61B 5/107; A61B 5/1072; A61B 5/1075; A61B 5/1079; G01B 11/02; G01B 11/022; G01B 11/026; G01B 11/14
USPC ........ 382/100, 103, 106, 115–118, 154, 190, 382/195, 224, 282, 285, 286, 291, 325; 345/419, 660, 661, 667; 351/204
See application file for complete search history.

(56) References Cited

U.S. PATENT DOCUMENTS

| | | | |
|---|---|---|---|
| 6,995,762 | B1 | 2/2006 | Pavlidis et al. |
| 7,630,006 | B2 * | 12/2009 | DeLuca .................... G06T 7/90 348/241 |
| 9,265,414 | B2 | 2/2016 | Wilson et al. |
| 9,628,697 | B2 * | 4/2017 | Choukroun ............ G06V 40/19 |
| 9,727,787 | B2 | 8/2017 | Wilf et al. |
| 10,610,097 | B2 | 4/2020 | Breuninger et al. |
| 10,799,112 | B2 * | 10/2020 | Predham ................. A61B 3/111 |
| 10,997,794 | B2 * | 5/2021 | Kelly ...................... G06T 7/60 |
| 2010/0220285 | A1 | 9/2010 | Simmonds |
| 2012/0093372 | A1 * | 4/2012 | Liu .......................... G06T 7/50 382/106 |
| 2012/0269407 | A1 | 10/2012 | Criminisi et al. |
| 2015/0078631 | A1 | 3/2015 | Belhumeur et al. |
| 2015/0163036 | A1 | 6/2015 | Thomas et al. |
| 2017/0111895 | A1 | 4/2017 | Tiirola et al. |
| 2018/0331794 | A1 | 11/2018 | Nagaraja et al. |
| 2019/0357264 | A1 | 11/2019 | Yi et al. |

OTHER PUBLICATIONS

P. Caroline, "The Effect of Corneal Diameter on Soft Lens Fitting," blog entry on www.contamac-globalinsight.com, originally posted Nov. 17, 2016.
T.F. Cootes et al., "Active appearance models," IEEE Transactions on Pattern Analysis & Machine Intelligence 23, pp. 681 to 685, doi:10:1109/34:927467, 2001.
T.M. Cover et al., :Elements of Information Theory, Wiley-Interscience, USA, 1991.
N. Dalal et al., "Histograms of oriented gradients for human detection," IEEE Computer Society Conference on Computer Vision and Pattern Recognition (CVPR'05), pp. 886 to 893 vol. 1. doi:10:1109/CVPR:2005:177, 2005.
C. DING et al., "Minimum redundancy feature selection from microarray gene expression data," Computational Systems Bioinformatics, Proceedings of the 2003 IEEE Bioinformatics Conference. CSB2003, pp. 523 to 528, 2003.
N.A. Dodgson, "Variation and extrema of human interpupillary distance," Stereoscopic Displays and Virtual Reality Systems XI 5291, pp. 36 to 46, 2002.
C. C. Gordon et al., "2012 Anthropometric Survey of U.S. Army Personnel: Methods and Summary Statistics," 2012, statistics (No. NATICK/TR-15/007); Army Natick Soldier Research Development and Engineering Center MA, http://www.dtic.mil/dtic/tr/fulltext/u2/a611869.pdf. Retrieved Jun. 2017.
W. Hastings, "Monte Carlo sampling methods using Markov chains and their applications," Biometrika vol. 57, pp. 97 to 109, 1971.
Industrial Norm "Ophthalmic optics—Spectacle lenses—Vocabulary (ISO 13666:2012)," German and English version EN ISO 13666:2012, Oct. 2013.
D.E. King, "Dlib-ml: A Machine Learning Toolkit," Journal of Machine Learning Research 10, pp. 1755 to 1758, 2009.
S. Pathi et al., "A Novel Method for Estimating Distances from a Robot to Humans Using Egocentric RGB Camera" Sensors, vol. 19, No. 14, pp. 1 to 13, Jul. 17, 2019.
F. Pedregosa et al., "Scikit-learn: Machine learning in Python," Journal of Machine Learning Research 12, pp. 2825 to 2830, 2011.
H. Peng et al., "Feature selection based on mutual information criteria of max-dependency, max-relevance, and min-redundancy," IEEE Transactions on Pattern Analysis and Machine Intelligence 27, pp. 1226 to 1238, 2005.
C. Rasmussen et al., "Gaussian Processes for Machine Learning," Adaptive Computation and Machine Learning, MIT Press, Cambridge, MA, USA, 2006.
A. Rosebrock "Facial Landmarks with Dlib, OpenCV and Python," posted on www.pyimagesearch.com on Apr. 3, 2017.
K. Shashi et al., "Face distance estimation from a monocular camera," 2013 IEEE International Conference on Image Processing, pp. 3532 to 3536, Sep. 15, 2013.
B. Winn et al., "Factors Affecting Light-Adapted Pupil Size in Normal Human Subjects," Investigative Ophthalmology & Visual Science, pp. 1132 to 1137, 1994.
International Search Report and Written Opinion issued in PCT/EP2021/056528, to which this application claims priority, dated Mar. 29, 2021.
International Preliminary Report on Patentability issued in PCT/EP2021/056528, to which this application claims priority, dated Jun. 20, 2022.
Gower, "Generalized procrustes analysis," Psychometrika 40, pp. 33 to 51, Mar. 1975.
Bradski, "The OpenCV Library," Dr. Dobb's Journal of Software Tools, 120; pp. 122 to 125, Nov. 2000.
Non-final Office action by the USPTO issued in U.S. Appl. No. 18/066,428, which is a continuation hereof, dated Aug. 2, 2023.

* cited by examiner

COMPUTER IMPLEMENTED METHODS AND DEVICES FOR DETERMINING DIMENSIONS AND DISTANCES OF HEAD FEATURES

CROSS REFERENCE TO RELATED APPLICATIONS

This application is a continuation application of international patent application PCT/EP2021/056528, filed on Mar. 15, 2021, which claims priority to European patent application 20 163 342.7, filed on Mar. 16, 2020, both of which are hereby incorporated by reference in their entireties.

TECHNICAL FIELD

The present application relates to computer implemented methods and devices for determining dimensions or distances of head features based on one or more images of the head.

BACKGROUND

Various applications in the field of spectacle lens fitting or spectacle frame fitting require knowledge of dimensions of various features of the head. For example, the interpupillary distance (PD) as defined in 5.29 of DIN EN ISO 13666: 2013-10, which is the distance between the centers of the pupils when the eyes are fixating an object at an infinite distance in the straight-ahead position, may be needed both for customizing spectacle frames and in some instances also for adapting the spectacle lenses themselves to a particular person.

Many recent approaches using techniques like virtual fitting of spectacle frames rely on one or more images taken from a head of a person.

When taking an image of a head of a person, various dimensions of features of the head like interpupillary distance may be determined in pixels (picture elements). However, some scale is needed to convert this size in pixels to the real-world size, for example in millimeters.

In the following, the term "real dimension" will be used to refer to dimensions of a feature in the real world (in millimeters, centimeters etc.), in contrast to the dimensions given in pixels, which can be taken directly from the image and will be referred to as "pixel dimension."

The term "feature" in this respect refers to one or more parts of a head which may be identified in the image, and/or relationships between such parts. For example, the interpupillary distance may be seen as such a feature, as well as single parts like the nose, ears, eyes etc.

A plurality of conventional approaches for obtaining such a scale are known. For example, U.S. Pat. No. 9,265,414 B2 uses an object of known size which is captured together with other objects in an image. For example, the object of known size may be a plastic credit card which is held against the head to be captured with an image, and then the number of pixels in the image spanned by the credit card (its real dimensions) is determined. As the real dimensions of the credit card (for example in millimeters) are also known, this corresponds to a scale which enables the conversion of a dimension in pixels to a dimension in millimeters.

Another publication which uses a reference object of a known size, in this case for a virtual try-on technology, is U.S. Pat. No. 6,535,233. These approaches require the object of known size, which may be inconvenient in some cases.

U.S. Pat. No. 6,995,762 B1 enables solid object reconstructions of objects found in two-dimensional images. This approach requires knowledge of the exact physical size of the imaged object.

U.S. Pat. No. 6,262,738 B1 describes a method to estimate volumetric distance maps from two-dimensional images. The method uses physical rays projected in parallel and perpendicular to the object in three-dimensional space and then reconstructs the size estimates from the resulting two-dimensional image. For this approach, the specific rays for obtaining depth images are required.

JP6392756B2 discloses a method for estimating a size of an object by taking multiple images while the object to be measured is rotated on a platform with a known rotation axis and a known rotation rate. For this approach, the rotating platform is required.

In another approach, which is disclosed in U.S. 2010/0220285 A1, the distance between a camera used for capturing an image of a head of a person and the head is measured, for example by using an ultrasonic sensor. When knowing the distance and the pixel dimension of a feature in an image, the real dimension for example in millimeters may be calculated for a given optic of the camera. In other words, for a specific camera having a specific optic, the pixel dimension of a feature depends on the distance of the feature from the camera and the real dimension of the feature. If two of the three quantities i.e., pixel dimension, real dimension of a feature (for example in millimeters) and distance of the camera from the feature are known, the third one may be calculated.

For some applications, it is also required to determine the distance of the feature, in particular an eye, from the camera, for example for eccentric photorefraction measurements as described in WO2018/002332 A2.

Kumar M S Shashi et al., "Face distance estimation from a monocular camera," 2013 IEEE International Conference on Image Processing, 2013-09-15, pages 3532-3536, XP032966333, DOI: 10.1109/ICIP.2013.6738729, Sai Krishna Pathi et al., "A Novel Method for Estimating Distances from a Robot to Humans Using Egocentric RGB Camera" Sensors Vol 19, No. 14, 2019-07-17, pages 1-13, XP055725398, DOI: 10.3390/s19143142, and Bianco Simone et al., "A unifying representation for pixel-precise distance estimation," Multimedia Tools and Applications, Kluwer Academic Publishers, Boston, US, Vol. 78 No. 10, 2018-08-24, pages 13767-13786, XP036807892, ISSN: 1380-7501, DOI: 10.1007/S11042-018-6568-2, each disclose methods for estimating a distance between a camera and a face based on facial features.

As can be seen from the above explanations, conventional approaches to determine real dimensions of features in an image or to determine the distance of the feature from the camera when taking the image have various drawbacks, like requiring specific devices like rotating platforms or specific illumination rays, multiple images or additional objects of known dimensions.

SUMMARY

Therefore, it is an object of the present application to provide methods and corresponding devices for determining real dimensions or distances of head features which do not require special additional hardware or the taking of multiple images.

This object is achieved by a method for estimating or determining dimensions or distances of head features and a corresponding device as disclosed herein. Exemplary embodiments, as well as computer programs, and storage mediums or data signals carrying such computer programs are disclosed below.

According to the disclosure, a computer implemented method for determining dimensions or distances of head features is provided. The method comprises:

providing an image of a head of a person, identifying a plurality of features in the image, and estimating at least one of a real dimension of at least one target feature of the plurality of features or a real distance between at least one target feature of the plurality of features and a camera device used for capturing the image based on a probability distribution for a real dimension of at least one feature of the plurality of features and a pixel dimension of the at least one feature of the plurality of features.

As already mentioned, "real" dimensions and "real" distances are dimensions and distances in the real world, for example the pupil distance of a person in millimeters. Pixel dimensions refer to dimensions as can be taken directly from the image. For example, a pixel dimension corresponding to the interpupillary distance is the distance in pixels between the pupils as found in the image.

"At least one target feature of the plurality of features" refers to the feature or features for which the real dimension or real distance is to be determined. "At least one feature of the plurality of feature" refers to the feature or features used as a basis for this determination. The two are not mutually exclusive, i.e., a feature may be both "at least one target feature of the plurality of features" and "at least one feature of the plurality of features," but it is also possible to use different features as a basis for the determination and as target feature(s).

A probability distribution in the sense of this application is an information, in particular a mathematical function that gives information about the probabilities of occurrence of different real dimensions of the features. It may be a function the integral of which is normalized to 1 to give probabilities in the mathematical sense. A probability distribution constitutes prior knowledge about the real dimensions of a feature. Such probability distributions may be obtained using data measured from many heads. Generally, dimensions of the human body including the head, in particular, the face, have been examined in medicine and biology for a long time, and therefore extensive data and probability distributions are available and have been published. Examples for such publications include Patrick Caroline, "The Effect of Corneal Diameter on Soft Lens Fitting," Nov. 17, 2016; blog on www.contamac-globalinsight.com, C. C. Gordon et al., "2012 Anthropometric Survey of U.S. Army Personnel: Methods and Summary Statistics," 2012, statistics (No. NATICK/TR-15/007); Army Natick Soldier Research Development and Engineering Center MA. Retrieved June, 2017, from www.dtic.mil/dtic/tr/fulltext/u2/a611869.pdf; B. Winn et al., "Factors Affecting Light-Adapted Pupil Size in Normal Human Subjects," Investigative ophthalmology & visual science 1994; or NA Dodgson, "Variation and extrema of human interpupillary distance," Stereoscopic Displays and Virtual Reality Systems XI 5291, 36-46, 2002.

In other exemplary embodiments, physically motivated mathematical models may be used as probability distribution functions. For example, if it is known that the distribution of sizes of an object (e.g., an ear) is very well described by a Gaussian normal distribution, then that mathematical function (in this case Gaussian normal distribution) may be used as the probability distribution, without needing to model a complete probability distribution from available data, or the distributions may be measured by a provider of a computer program realizing the above-mentioned computer implemented method in advance, in which case also covariances between distributions of different dimensions of different features may be measured. These covariances may then be used later, as will be described further below. In other words, if the provider of the program obtains the probability distributions himself, e.g., by measuring features on a large number of heads or faces, covariances between dimensions of different features may also be determined (e.g., whether or not large heads correlated with large ears). It should be noted that when using different approaches to obtain the probability distributions as mentioned above, the obtained probability distributions will also vary, depending on the data on which they are based. This may lead to correspondingly varying results of the estimating of the real dimension or real distance.

By using a single probability distribution of only a single feature, i.e., if the at least one feature of the plurality of features is only a single feature. a rough estimation of the real dimension of the target feature and therefore of the real distance would be possible (essentially, one could say that the maximum of the probability distribution of the single feature is the most likely real dimension of the feature).

Therefore, typically probability distributions of a respective real dimension of at least two features are used, i.e., the at least one feature of the plurality of features is at least two features. In this way, the estimation may be refined, such that a high accuracy may be obtained.

In this way, just using the image and available data, an estimation of the at least one of the real dimension or real distance may be performed. In this respect, as already explained in the introductory portions, real dimensions of features in the image and the distance between the features and a certain camera device having a certain optic have a fixed relationship.

Identifying a plurality of features in the image may be performed in a conventional manner, using Dlib or open CV software to detect facial features (see for example article "Facial Landmarks with Dlib, OpenCV and Python" by Adrian Rosebrock, Apr. 3, 2017, on www.pyimagesearch.com, G. Bradski, "The OpenCV Library," Dr. Dobb's Journal of Software Tools, 2000, or D. E. King, "Dlib-ml: A Machine Learning Toolkit," Journal of Machine Learning Research), or by using other conventional facial segmentation software, or by using a more complex e.g., machine learning compressed representation of the face. In such a compressed version, dimensions measured are not immediately apparent in terms of human defined measurements, but may be processed by machine learning techniques.

Another approach for identifying a plurality of features start with detecting a face of a person in the image. This may be performed using any conventional face detection method, for example the method described in Dalal, N., Triggs, B., "Histograms of oriented gradients for human detection, in: 2005 IEEE Computer Society Conference on Computer Vision and Pattern Recognition (CVPR'05), pp. 886-893 vol. 1. doi:10:1109/CVPR: 2005:177.

In this method for face detection an image pyramid is constructed and a histogram of oriented gradients is used to extract features from a window sliding across the image. From these features a linear support vector machine classifier is trained, which classifies each window as either containing a face or not.

Then, in the currently discussed approach, an active appearance model (AAM), as described for example in Cootes, T. F., Edwards, G. J., Taylor, C. J., 2001. Active appearance models. IEEE Transactions on Pattern Analysis & Machine Intelligence 23, 681-685. doi:10:1109/34: 927467 is applied to the image once the face has been detected to detect so-called landmarks. With the landmark detection various points on the face are identified which can be labelled, for example, the ears and the top and bottom of the ears, the boundary of the lips, eyes and irises. AAM is a class of generative models which builds upon a statistical, parametrized notion of a deformable object and is composed of two parts: a shape model and an appearance model. The shape model, also called point distribution model, defines an object as the array of landmark coordinates.

During its training, the shapes of all objects of interest in the training set are aligned and normalized for example through the generalized Procrustes analysis as described in Gower, J. C., 1975. Generalized procrustes analysis. Psychometrika 40, 33-51. In this application the objects of interest are the detected faces. Afterwards an orthonormal basis for this set of shapes may be computed using principle component analysis (PCA). An object s can thus be defined by the shape model as:

$$s = \bar{s} + Sp \qquad (1)$$

where $\bar{s}$ represents the mean shape, p are the shape parameters specific for this one object and S are the principal components of the shapes.

The appearance model includes information on the texture of the image around the defined landmarks and its training process is very similar to that of the shape model.

The first step is to extract information from the training images, which in this specific application consists of the image gradient orientation. Next, all of the images are warped onto the mean shape, such that the pixels for corresponding landmarks for all the images are aligned. With the images aligned, it is then possible to compute the principal components of the appearance, using PCA. Finally, patches around the landmarks are selected and the remaining information is discarded.

The appearance a of a face can then be defined in vector notation, similarly to the shape model, as:

$$a = \bar{a} + Ac \qquad (2)$$

where $\bar{a}$ defines the mean appearance for all training images, c are the appearance parameters for this image and A are the principal components of the appearance.

The next step of the currently described feature detection approach is then to fit the model to a new image. This is equivalent to finding the optimal set of parameters p and c that minimize the difference between the image texture sampled from the shape model and the appearance model. In other words, given an image I containing the object of interest and an initial guess for the object shape s, then the difference r between the current appearance $\bar{a}+Ac$ and the image texture, sampled at the points in s, $A_s$, can be defined as $r = A_s - (\bar{a}+Ac)$. Then the optimal model parameters are given by:

$$p^*, c^* = \arg\min_{p,c} \|A_s - (\bar{a}+Ac)\| \qquad (3)$$

This cost function can be optimized with any optimization algorithm, such as the ones in the family of gradient descent.

From the thus obtained landmarks, then features may be determined. In particular, features may be pixel dimensions between landmarks identified. For example, once the facial landmarking model described above is applied to an image, a set of N landmark points are generated. A set of M=N(N−1)/2−1 unique, but correlated, features having pixel dimension measures on the face can be constructed from the set of N landmark points.

Typically, two or more of the following features are identified, and the pixel dimensions are determined:
the interpupillary distance (PD),
the diameter of one or both irises of the eyes,
the diameter of the pupils of the eyes,
the vertical length of the ears,
the width of one eye or both eyes,
the height of the head,
the distance between the bottom of the chin and the middle of the nose between the eyes, which is referred to as Menton-Sellion distance,
the bizygomatic breadth, which is the widest point across the face measured at the top of the jaw, and/or
the Euryon breadth, which is the maximal width of the forehead above the ears.

The above features may be easily obtained using the above-mentioned image analysis techniques and are well documented, such that probability distributions are available, or can be obtained.

In some exemplary embodiments, the pixel dimensions may be normalized to the pixel dimensions of one of the features. For example, some exemplary embodiments aim at ultimately determining the interpupillary distance of a person based on an image of the person, and in such a case the pixel dimensions may be normalized by the interpupillary distance as measured in pixel space, such that the features used from here forward are dimensionless and don't depend on the size of the image. The normalized pixel dimensions may facilitate later processing and may be identified as an input feature to be used by subsequent machine learning algorithms.

In some exemplary embodiments, an automatic or manual selection of features may be performed. As mentioned above, for N landmark points M=N(N−1)/2−1 features (distances between points) may be determined. Already for N=88, M=3827 potential input features would result. To reduce this number, feature selection techniques may be applied, to identify a subset of S features from the M features.

For example the Minimum Redundancy—Maximum Relevance (MRMR) algorithm may be employed to reduce the feature set. This algorithm is described for example in Ding, C., Peng, H., 2003. Minimum redundancy feature selection from microarray gene expression data, in: Computational Systems Bioinformatics, Proceedings of the 2003 IEEE Bioinformatics Conference. CSB2003, pp. 523-528. doi:10: 1109/CSB: 2003:1227396 or in Peng, H., Long, F., Ding, C., 2005, Feature selection based on mutual information criteria of max-dependency, max-relevance, and min-redundancy. IEEE Transactions on Pattern Analysis and Machine Intelligence 27, 1226-1238. doi:10:1109/TPAMI: 2005:159. The MRMR algorithms performs feature selection by identifying those features which provide the most information about a target feature, and are therefore the most correlated, while simultaneously discarding the features which are redundant with each other, i.e., those that are most correlated with other features. The mutual information (MI) as described in Cover, T. M., Thomas, J. A., 1991, Elements of Information Theory. Wiley-Interscience, USA may be used as the correlation metric for measuring relevance and redundancy. The target feature is a feature that ultimately is to be determined from an image of a person, for example the interpupillary distance (PD) to be used for fitting a spectacle frame.

An exhaustive search of the entire combinatorial space of features would be computationally expensive. As described in Peng et al. cited above, a greedy forward-search algorithm may be implemented. The initial set of features is ranked by the value of the MI with the interpupillary distance and the top P features are selected, where P>S and P<<M. This set of P features is then analyzed to identify a final feature set S. Features are added from P to S if the feature both maximizes the total relevance with the target feature, while minimizing the total redundancy with other features already in S. In practice, at each step of increasing the feature set to size S, the feature leading to the largest mutual information difference $d_{MI}$, is added. The quantity $d_{MI}$ is defined as $$d_{MI} = \frac{1}{|S|}\sum_{i \in S} I(i, PD) - \frac{1}{|S|^2}\sum_{i \in S}\sum_{j \in S \setminus i} I(i, j) \quad (4)$$

where S is the set of features, PD is the interpupillary distance in mm taken as an example target feature here and I(_;_) is the mutual information operation.

A final feature vector of a size may be chosen to allow an estimation of the co-variance matrix from the relatively small amount of labelled data, for example S=20.

In one aspect of the disclosure, based on the pixel dimensions as well as the probability distributions of the identified features, a probability distribution P(pix per mm|d, θ) for the number of pixels per millimeter pix per mm as estimated from features in an image may be obtained according to equation (5) below:

i) $P(pix\ per\ mm|d,\theta) \propto \Pi_{i=1}^{N} P(d_i|pix\ per\ mm,\theta_i)\pi(\theta_i)$ (5)

In equation (5), $d_i$ is the number of pixels spanning an i=1, 2, ..., Nth feature of the at least one feature of the plurality of features or, in other words, the pixel dimension of the i-th feature. $\pi(\theta_i)$ represents the probability distribution of a real dimension $\theta_i$ of feature i and/or its covariances with other measured pixel dimensions. $P(d_i|pix\ per\ mm, \theta_i)$ is an operator yielding the likelihood of measuring $d_i$ based on pix per mm and θ for given $\pi(\theta_i)$. To explain further, here, $d_i$ is the number of pixels of the respective dimension of feature i in the plane of the face (a plane perpendicular to and essentially at the same physical distance from the camera device, which at least approximately is true for facial images), pix per mm is a variable which may be seen as a current or first estimation of how many pixels there are per millimeter, and $\theta_i$ is a size of feature i in physical units. $\pi(\theta_i)$ as probability distribution represents the prior knowledge about a size distribution of feature i and optionally its covariances (e.g., as mentioned above) with other measured pixel dimensions before measurements are made. $\theta_i$ may be calculated in real dimension (e.g., in millimeters) by multiplying $d_i$ by pix per mm.

In other words, $P(d_i|pix\ per\ mm, \theta_i)$ is the probability of seeing feature i as big or small in view of the measurements in pixels, given prior knowledge represented by $\pi(\theta_i)$. $\pi(\theta_i)$ may be obtained as explained above based on public databases, measurements etc. The underlying idea is that one looks at different values of pix per mm to determine what are reasonable values of pix per mm such that all of the features have reasonable sizes in real dimension. To give a very simplified numerical example, $\pi(\theta_i)$ may indicate that the probability of the real dimension $\theta_i$ of feature i being 2 mm is 0.25, being 3 mm is 0.5 and being 4 mm is 0.25. If $d_i$ is 6 pixels, the probability for an estimate of 2 pixels per mm based on feature i is 0.5, for 3 pixel per mm 0.25 and for 1.5 pixel per mm also 0.25. This is only a very simple numerical example. Equation (5) now combines such estimates for a plurality of features i.

In another aspect of the disclosure, P(pix per mm|d, θ), a probability distribution for the number of pixels per millimeter, as measured using features in an image based on d and θ for a feature to be measured, is calculated. P(pix per mm|d, θ) is usable for any target feature in the image and may be estimated based on, either from an MCMC (Monte Carlo Markov Chain) type exploration of probability space or a mathematical combination of probability distributions in other exemplary embodiments. Equation (5) gives such a mathematical combination by multiplication. In particular, when there is a plurality of probability distributions involved, the calculation is a higher dimensional computation which requires a high amount of computing power, memory or both. In such cases, the probability distributions may be sampled in a certain manner, for example, using the above mentioned MCMC approach which is a standard way of solving such problems in statistics. This approach is for example described in W. Hastings, Monte Carlo sampling methods using Markov chains and their applications, Biometrika Vol. 57, pp. 97 to 109.

With a single measurement of a single feature (e.g., i=1), P(pix per mm|d, θ) may only be based on $\pi(\theta_i)$ (i=1) but with increasing number of measurements (i>1), P(pix per mm|d, θ) becomes more accurate (e.g., by using dimensions of a plurality of features). ∝ indicates proportionality.

Essentially, equation (5) says that you have some prior information $\pi(\theta_i)$ and you can obtain an estimation P(pix per mm|d, θ).

Another approach to determining P(pix per mm|d, θ) and ultimately a size of a target feature like the interpupillary distance is using machine learning techniques including the scikit-learn as described in Pedregosa, F., Varoquaux, G., Gramfort, A., Michel, V., Thirion, B., Grisel, O., Blondel, M., Prettenhofer, P., Weiss, R., Dubourg, V., Vanderplas, J., Passos, A., Cournapeau, D., Brucher, M., Perrot, M., Duchesnay, E., 2011. Scikit-learn: Machine learning in Python. Journal of Machine Learning Research 12, 2825-2830, implementations of K-Nearest Neighbors and Gaussian processes as described in Rasmussen, C., Williams, C., 2006. Gaussian Processes for Machine Learning. Adaptive Computation and Machine Learning, MIT Press, Cambridge, Mass., USA for regression may be used.

In case of the interpupillary distance as a target feature, p(PD|X(face), S) may be computed for a given face shape X(face), i.e., a probability distribution for the real dimension of the interpupillary distance. p(PD|X(face) may be seen as a special case of equation (5) above, specific for the target feature, in this case the interpupillary distance PD. An example for the determination will be given for the Gaussian process below. The Gaussian process allows the use of prior information in regions of data space where there is no training data. It also provides full probability distribution functions for the predicted values, rather than just point predictions. As input data, the features and information about the real dimensions of the features is used.

The goal of a Gaussian processes is to model the properties of functions by generalizing the Gaussian distribution. That is, assuming that the data consists of features X which are measured from a face image, then {X; PD} can be modelled through some unknown function f, with some added noise such that $PD_i = f(x_i) + \varepsilon$ (here the input X will be the face shape vectors and the outputs PD will be the inter pupil distances), then f can be seen as a random variable in itself. Here this variable will follow a multivariate Gaussian distribution, defined by its mean and covariance as:

$$f(x) = \aleph(m(x), \kappa(x,x')) \quad (6)$$

where m(x) defines the mean function and κ(x; x') is the kernel or covariance function.

$$m(x)=E[f(x)] \quad (7)$$

$$k(x;x')=E[(f(x)-m(x))(f(x')-m(x'))^T] \quad (8)$$

Generally the mean is set to zero, and the covariance should be chosen to be flexible enough to capture the data. Here, if the covariance is written in a matrix form as K, then the likelihood of the random variable f will be p(f|X)=ℵ(f|0,K). In effect this implies that the covariance between two input vectors x1 and x2 should be very similar to the covariance between their corresponding output values PD1 and PD2—in other words, two people with similar face shapes should have similar inter pupil distances.

The function f is initialized using a Gaussian distribution describing a prior on the interpupillary distance, e.g., prior information based on statistics on interpupillary distances. Data points are added to the Gaussian processes which update the distribution over f according to Bayes' theorem, as is shown in Eq. (9) below. This corresponds to the process of training the model with a labelled data set.

$$p(f|X, PD) = \frac{p(PD|f, X)p(f|X)}{\int p(PD|f)p(f|X)df} \quad (9)$$

Now that the distribution f has been constrained through training data, an estimate for the target value PD_ or a new input point x can be obtained. For that a predictive distribution is required. In the context of Gaussian Processes this will be a Gaussian distribution defined as follows:

$$f_*|X, PD, x_* \sim \aleph(\overline{f_*}, \text{cov}(f_*)) \quad (10)$$

$$\overline{f_*} = K(x_*, X)[K(X, X)+\sigma_n^2 I]^{-1}PD \quad (11)$$

$$\text{cov}(f_*) = K(x_*, x_*) - K(x_*, X)[K(X, X)+\sigma_n^2 I]^{-1}K(X, x_*) \quad (12)$$

where $\sigma_n^2$ defines the noise variance, assuming that the noise for each data point is independent of the others.

For the kernel K for example an exponential kernel, a linear kernel, a matern32 kernel, a matern52 kernel or linear combinations thereof may be used. Typically, an Exponential Quadratic Kernel is used, which has given good results and is defined as follows:

$$K(x_q, x_p) = \sigma_f^2 \exp\left(-0.5\sum_{d=1}^{D}\left(\frac{x_{q,d}-x_{p,d}}{l_d}\right)^2\right) + \sigma_n^2 \delta_{qp} \quad (13)$$

where l is the characteristic length-scale and $\sigma_f^2$ is the signal variance. The values for these parameters, as well as for $\sigma_n^2$ are set to their maximum likelihood estimates, which can be obtained using the optimization method provided by scikit-learn.

The Gaussian process or any other machine learning approach may be trained by training data, where the real dimensions are known (e.g., measured by other means), such that both the image with the pixel dimensions and the real dimensions of features from the training data are used to approximate the function describing the probability in equation (5).

Returning to equation (5), therefore, a scale which gives the number of pixels per millimeters in the image can be determined, and as a result, the real dimension of any feature, for example, the interpupillary distance, may be determined. With the above relationship between pixel dimensions, real dimensions and camera device information, also the distance from the camera device may be determined.

In some exemplary embodiments, the probability distributions (e.g., $\pi(\theta_i)$ in equation (5)) are selected based on additional information regarding the person. In this way, more specific probability distributions than general probability distributions for all humans may be used. Such additional information may for example include sex (male or female, or other gender score), ethnicity (Caucasian, Asian etc.), size or age. For example, when sex, age, and ethnicity are known, probability distributions specific to this combination may be used. Similar considerations apply to size. Such additional information may, for example, be input by the person or another user. In some exemplary embodiments, additional information may also be derived from the image. For instance, an estimate of ethnicity or sex may be obtained by image analysis.

In some exemplary embodiments, instead of a single image also a plurality of images may be used, and identifying the features in the plurality of images may be used to increase the accuracy.

The estimated real dimension or distance may then be used, for example, for fitting of spectacle frames, manufacturing of spectacle glasses or also eye examinations like the photorefraction mentioned initially.

Furthermore, a computer program is provided, which contains instructions that, when executed on a processor, cause execution of any of the methods above.

A corresponding storage medium, in particular tangible storage medium like a memory device, hard disk, DVD or CD storing such a computer program are also provided, as well as a data carrier signal transmitting such a computer program.

Furthermore, a corresponding device is provided, comprising:
means for providing an image of a head of a person,
means for identifying a plurality of features in the image, and
means for estimating at least one of a real dimension of at least one of the features and a real distance between at least one of the features from a camera device used for capturing the image based on a probability distribution for a real dimension of at least one feature of the plurality of features and a pixel dimension of the at least one feature.

The device may be configured to carry out any of the above methods.

Techniques as discussed above are not limited to applications to determine dimensions and distances related to features of the head, but may generally be used for determining real dimensions of features in an image. In such applications, compared to the above-discussed method and devices, the image of the head of the person is replaced by a general image, and the features in the image may be any objects in the image like trees, persons, cars etc. Also for such objects, probability distributions regarding dimensions are available, or can be measured. Additional information in this case may be, for example, a brand of a car, a species of a tree etc. Otherwise, techniques as discussed above may be applied.

BRIEF DESCRIPTION OF THE DRAWINGS

The disclosure will now be described with reference to the drawings wherein.

DESCRIPTION OF EXEMPLARY EMBODIMENTS

Figure 1:
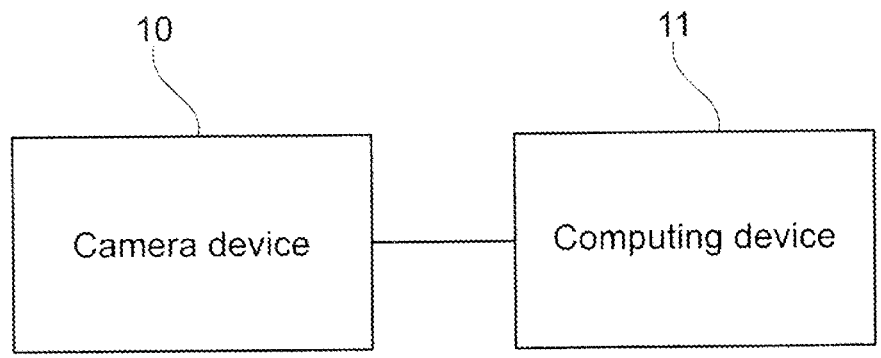
FIG. 1 is a block diagram of a device according to an exemplary embodiment.

FIG. 1 is a block diagram of a device according to an exemplary embodiment. The device of FIG. 1 comprises a camera device 10 and a computing device 11. Camera device 10 comprises one or more optical elements and an image sensor to capture an image of a head of a person. The image is provided to computing device 11. Computing device 11 includes one or more processors. Computing device 11 may be a personal computer, or may also comprise a plurality of separate entities communicating with each other to perform the method as will be described further below with respect to FIG. 2. In some exemplary embodiments, camera device 10 and computing device 11 may be integrated in a single device, for example, a smartphone or a tablet computer. For executing the method of FIG. 2 which will be described next, computing device 11 is programmed accordingly.

Figure 2:
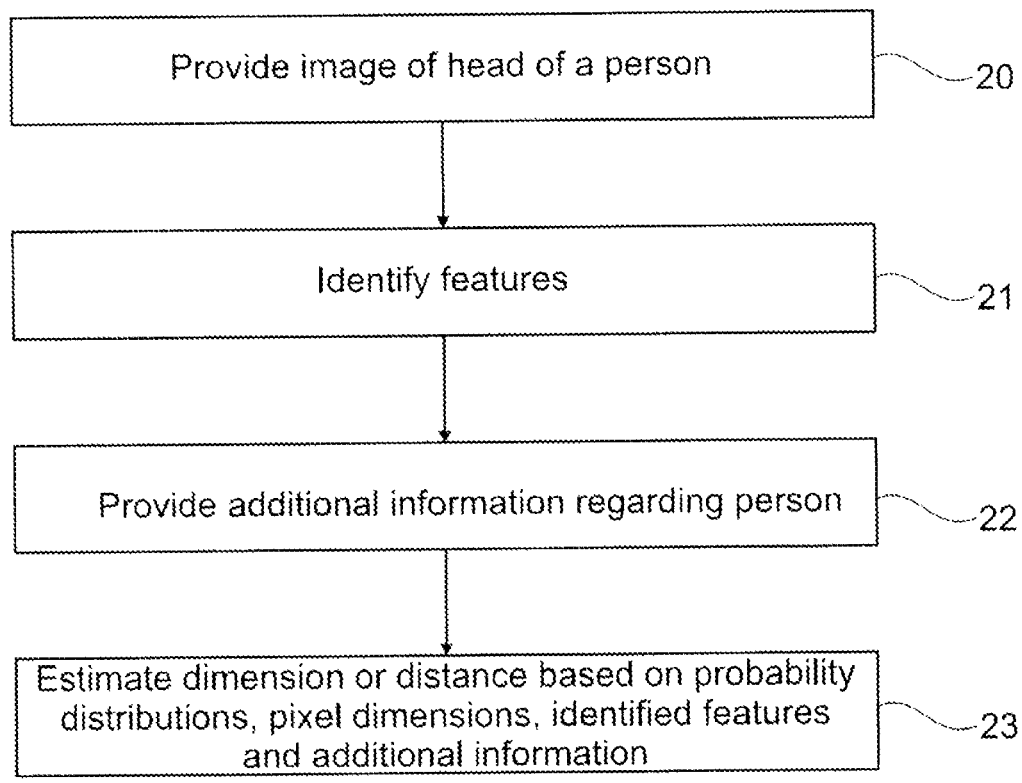
FIG. 2 is a flowchart illustrating a method according to an exemplary embodiment.

FIG. 2 is a schematic block diagram of one exemplary embodiment of the method of the present disclosure. At 20, an image of a head of a person is provided. In the exemplary embodiment of FIG. 1, the image is provided by camera device 10.

Figure 3:
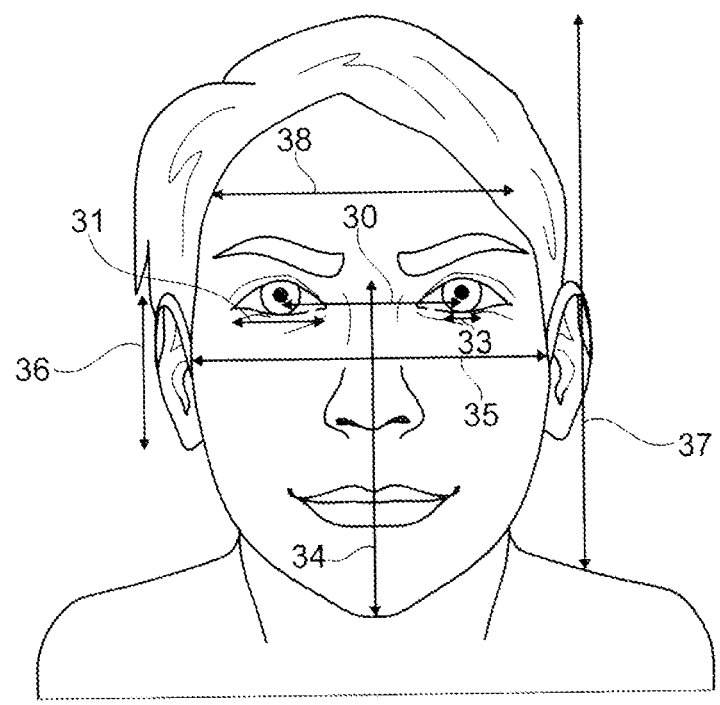
FIG. 3 is a diagram illustrating various features of a head of a person.

At 21, a plurality of features in the image are identified. Some examples for features are shown in FIG. 3. The features shown in FIG. 3 include the interpupillary distance 30, diameter of the iris 33, width of the eyes 31, vertical length of the ears 36, Menton-Sellion distance 34, bizygomatic breadth 35, Euryon breadth 38 or height of the head 37.

Returning to FIG. 2, at 22, additional information regarding the person is provided. As explained above, examples for such additional information include size, gender, age, ethnicity and the like.

At 23, at least one of a real dimension of at least one target feature of the plurality of features or a real distance between at least one target feature of the plurality of features from the camera device 10 based on probability distributions for real dimensions of at least one, typically at least two features of the plurality of features and pixel dimensions of at least one, typically at least two of the plurality of features, as described above, is estimated.

Figure 4:
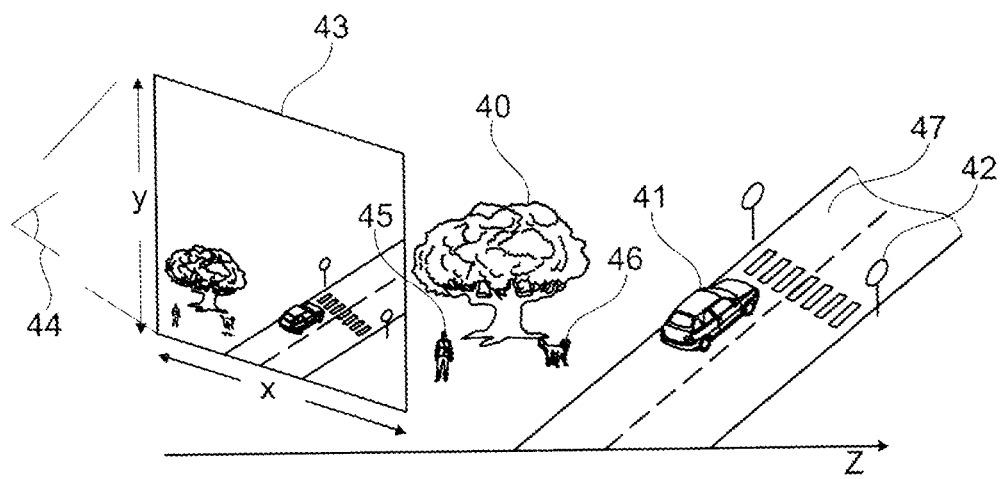
FIG. 4 illustrates various features in a landscape image.

As mentioned above, techniques discussed herein may be extended from head features as shown in FIG. 3 to dimension estimation of other features in images. An example is shown in FIG. 4. Here, a scene comprising a tree 40, a car 41, traffic signs 42, a person 45, a dog 46, and a street 47 are provided. For all these kinds of objects, typical dimensions or size probability distributions for dimensions exist. The pixel dimensions of these features or objects in an image 43 depend on their real dimension and a distance in z-direction from a camera device 44 taking the image 43. Using probability distributions and additional information, for example, species of tree 40, gender, ethnicity or age of person 45, race of dog 46, brand or type of car 41 etc., such real dimensions and/or distances in z-direction may be determined.

Some exemplary embodiments are defined by the following examples:

Example 1. A computer implemented method for estimating or determining dimensions or distances of head features, comprising:

providing (20) an image of a head of a person, identifying (21) a plurality of features (30-38) in the image, characterized by estimating (23) at least one of a real dimension of at least one target feature of the plurality of features (30-38) or a real distance between at least one target feature of the plurality of features (30-38) and a camera device (10) used for capturing the image based on a probability distribution for a real dimension of at least one feature of the plurality of features (30-38) and a pixel dimension of the at least one feature of the plurality of features (30-38).

Example 2. The method of example 1, characterized in that the at least one feature of the plurality of features comprises at least two features of the plurality of features.

Example 3. The method of example 1 or 2, characterized in that the features (30-38) comprise one or more features taken from, the group consisting of:

an interpupillary distance (30), an iris diameter (33), a pupil diameter, a vertical ear length (36), a Menton-Sellion distance (34), a bizygomatic breadth (35), an Euryon breadth (38), an eye width (31), and a head height (37).

Example 4. The method of any one of examples 1 to 3, characterized in that the estimating comprises calculating a probability distribution P(pix per mm|d, θ) for the number of pixels per millimeter pix per mm for the image according to i) $P(\text{pix per mm}|d, \theta) \propto \Pi_{i=1}^{N} P(d_i|\text{pix per mm}, \theta_i) \pi(\theta_i$ ii) where $d_i$ is the number of pixels spanning an i=1, 2, . . . , Nth feature, $\pi(\theta_i)$ represents the probability distribution of a real dimension $\theta_i$ of feature i and/or its covariances with other measured pixel dimensions, and $P(d_i|\text{pixel per mm}, \theta_i)$ is an operation giving the probability of the real dimension $\theta_i$ for d, for a value pix per mm given the probability distribution $\pi(\theta_i)$.

Example 5. The method of any one of examples 1-4, further comprising providing additional information regarding the person, and selecting the probability distributions based on the additional information.

Example 6. The method of example 5, characterized in that providing the additional information comprises receiving the additional information as a user input, and/or comprises determining the additional information based on the image.

Example 7. The method of example 5 or 6, characterized in that the additional information comprises one or more of a sex of the person, an age of the person, an ethnicity of the person or a size of the person.

Example 8. The method of any one of examples 1-7, wherein estimating at least one of a real dimension of at least one of the features (30-38) comprises estimating an interpupillary distance of the person.

Example 9. The method of any one of examples 1-8, characterized in that providing an image comprises providing a plurality of images, wherein the estimating (23) is done based on the plurality of images.

Example 10. The method of any one of examples 1-9, characterized by one or more of:

fitting a spectacle frame to the head of the person based on the estimating (23), manufacturing spectacle glasses based on the estimating (23) or performing an eye examination based on the estimating (23).

Example 11. A device, comprising:

means (10) for providing an image of a head of a person, means for identifying a plurality of features (30-38) in the image, characterized by means for estimating at least one of a real dimension of at least one of the features (30-38) or a real distance between at least one of the features (30-38) from a means (10) used for capturing the image based on a probability distribution for a real dimension of at least one feature of the plurality of features (30-38) and a pixel dimension of the plurality of features (30-38).

Example 12. A computer program comprising instructions which, when carried out on one or more processors, cause execution of the method of any one of examples 1-10.

Example 13. A data carrier comprising the computer program of example 12.

Example 14. A data signal carrying the computer program of example 12.

Example 15. A device (11) comprising at least one processor and the computer program of example 12 stored for execution on the at least one processor.

The foregoing description of the exemplary embodiments of the disclosure illustrates and describes the present invention. Additionally, the disclosure shows and describes only the exemplary embodiments but, as mentioned above, it is to be understood that the disclosure is capable of use in various other combinations, modifications, and environments and is capable of changes or modifications within the scope of the concept as expressed herein, commensurate with the above teachings and/or the skill or knowledge of the relevant art.

The term "comprising" (and its grammatical variations) as used herein is used in the inclusive sense of "having" or "including" and not in the exclusive sense of "consisting only of." The terms "a" and "the" as used herein are understood to encompass the plural as well as the singular.

All publications, patents and patent applications cited in this specification are herein incorporated by reference, and for any and all purposes, as if each individual publication, patent or patent application were specifically and individually indicated to be incorporated by reference. In the case of inconsistencies, the present disclosure will prevail.

The invention claimed is:

1. A computer implemented method for determining dimensions or distances of head features, the method comprising:

provinding an image of a head of a person;

identifying a plurality of features in the image; and estimating at least one of a real dimension of at least one target feature of the plurality of features or a real distance between at least one target feature of the plurality of features and a camera device used for capturing the image based on a probability distribution for a real dimension of at least one feature of the plurality of features and a pixel dimension of the at least one feature of the plurality of features, wherein the estimating includes calculating a probability distribution P(pix per mm|d, θ) for a number of pixels per millimeter pix per mm for the image according to $$P(pix\ per\ mm|d, \theta) \propto \prod_{i=1}^{N} P(d_i|pix\ per\ mm, \theta_i)\pi(\theta_i)$$

where $d_i$ is a number of pixels spanning an i=1, 2, ..., Nth feature of the plurality of features, $\pi(\theta_i)$ represents a probability distribution of a real dimension $\theta_i$ of feature i and/or its covariances with other measured pixel dimensions, and $P(d_i|\text{pixel per mm}, \theta_i)$ is an operator yielding a likelihood of measuring $d_i$ based on pix per mm and $\theta_i$ for a given $\pi(\theta_i)$.

2. The method of claim 1, wherein the at least one feature of the plurality of features comprises at least two features of the plurality of features.

3. The method of claim 1, wherein calculating the probability distribution for the number of pixels per millimeter for the image is based on a Monte Carlo Markov Chain type exploration of probability space.

4. The method of claim 1, wherein the plurality of features includes one or more features selected from the group consisting of:

an interpupillary distance, an iris diameter, a pupil diameter, a vertical ear length, a Menton-Sellion distance, a bizygomatic breadth, an Euryon breadth, an eye width, and a head height.

5. The method of claim 1, further comprising providing additional information regarding the person, and selecting probability distributions based on the additional information.

6. The method of claim 5, wherein providing the additional information comprises receiving the additional information as a user input, and/or determining the additional information based on the image.

7. The method of claim 5, wherein the additional information comprises one or more of a sex of the person, an age of the person, an ethnicity of the person, or a size of the person.

8. The method of claim 1, wherein estimating a real dimension of at least one target feature of the plurality of features comprises estimating an interpupillary distance of the person.

9. The method of claim 1, wherein providing an image comprises providing a plurality of images, and wherein estimating is done based on the plurality of images.

10. The method of claim 1, further comprising:

fitting a spectacle frame to the head of the person based on the estimating;

manufacturing spectacle glasses based on the estimating; or performing an eye examination based on the estimating.

11. A computer program stored on a non-transitory data carrier and comprising instructions which, when carried out on one or more processors, cause execution of the method of claim 1.

12. A device comprising at least one processor and the computer program of claim 11 stored for execution on the at least one processor.

13. A device, comprising:

a camera device for providing an image of a head of a person;

an analyzing unit for identifying a plurality of features in the image; and a calculation unit for estimating at least one of a real dimension of at least one target feature of the plurality of features or a real distance between the at least one target feature of the plurality of features from the camera device used for capturing the image based on a probability distribution for a real dimension of at least one feature of the plurality of features and a pixel dimension of the at least one feature of the plurality of features, the estimating including calculating a probability distribution P(pix per mm|d, θ) for a number of pixels per millimeter pix per mm for the image according to $$P(pix \text{ per } mm | d, \theta) \propto \prod_{i=1}^{N} P(d_i | pix \text{ per } mm, \theta_i) \pi(\theta_i)$$

where $d_i$ is a number of pixels spanning an i=1, 2, ..., Nth feature of the plurality of features, $\pi(\theta_i)$ represents a probability distribution of a real dimension $\theta_i$ of feature i and/or its covariances with other measured pixel dimensions, and $P(d_i|\text{pixel per mm}, \theta_i)$ is an operator yielding a likelihood of measuring $d_i$ based on pix per mm and $\theta_i$ for given a given $\pi(\theta_i)$.

* * * * *